US012723033B2

(12) United States Patent
Narula et al.

(10) Patent No.: US 12,723,033 B2
(45) Date of Patent: Sep. 1, 2026

(54) FURAN COMPOUND AND ITS USE IN FRAGRANCE FORMULATIONS

(71) Applicant: INTERNATIONAL FLAVORS & FRAGRANCES INC., Union Beach, NJ (US)

(72) Inventors: Anubhav P.S. Narula, Hazlet, NJ (US); Zhe Guo, Freehold, NJ (US); Ana María Collada Pérez, Benicarló (ES)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 367 days.

(21) Appl. No.: 18/695,426

(22) PCT Filed: Oct. 10, 2022

(86) PCT No.: PCT/US2022/046190

§ 371 (c)(1),
(2) Date: Mar. 26, 2024

(87) PCT Pub. No.: WO2023/064220

PCT Pub. Date: Apr. 20, 2023

(65) Prior Publication Data

US 2024/0391891 A1 Nov. 28, 2024

Related U.S. Application Data

(60) Provisional application No. 63/256,146, filed on Oct. 15, 2021.

(51) Int. Cl.

| | |
|---|---|
| ***C07D 307/77*** | (2006.01) |
| ***A61K 8/49*** | (2006.01) |
| ***A61Q 13/00*** | (2006.01) |
| ***C11B 9/00*** | (2006.01) |

(52) U.S. Cl.

CPC .......... *C07D 307/77* (2013.01); *A61K 8/4973* (2013.01); *A61Q 13/00* (2013.01); *C11B 9/0076* (2013.01)

(58) Field of Classification Search

CPC ........................... C07D 307/77; A61K 8/4973; A61K 2800/10; A61Q 13/00; C11B 9/0076

See application file for complete search history.

(56) References Cited

FOREIGN PATENT DOCUMENTS

EP 3103431 A1 12/2016

OTHER PUBLICATIONS

International Search Report and Written Opinion—PCT/US2022/046190—mailed Jan. 20, 2023.

*Primary Examiner* — Andrew J. Oyer

(57) ABSTRACT

The present invention relates to a novel furan compound, 2,2,6,6,7,8,8-heptamethyl-3,3a,4,5,5a,6,7,8-octahydro-2H-indeno[4,5-b]furan, and its use as a fragrance material.

17 Claims, No Drawings

FURAN COMPOUND AND ITS USE IN FRAGRANCE FORMULATIONS

STATUS OF RELATED APPLICATION

This application if a 371 of International Patent Application No. PCT/US2022/046190, filed Oct. 10, 2022, and claims priority to U.S. Provisional Patent Application No. 63/256,146, filed Oct. 15, 2021, the contents of each which is hereby incorporated by reference as if set forth in its entirety.

FIELD OF THE INVENTION

The present invention relates to a new chemical entity and its use in providing enhanced and synergistic odor properties in certain fragrance formulations.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides a novel furan compound and its unexpected advantageous use in enhancing, improving or modifying the fragrance of perfumes, colognes, toilet water, fabric care products, personal products and the like.

More specifically, the present invention relates to a novel compound, 2,2,6,6,7,8,8-heptamethyl-3,3a,4,5,5a,6,7,8-octahydro-2H-indeno[4,5-b]furan, represented by Formula I set forth below:

Formula I

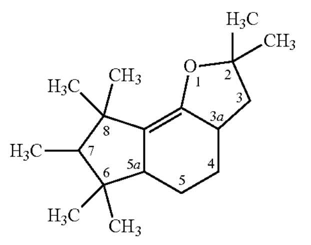

Another embodiment of the present invention relates to a fragrance formulation comprising the compound of Formula I.

Another embodiment of the present invention relates to a fragrance formulation comprising the compound of Formula I and 2,2,6,6,7,8,8-heptamethyldecahydro-2H-indeno[4,5-b]furan.

Another embodiment of the present invention relates to a fragrance formulation comprising the compound of Formula I in an amount of about 0.1% or higher by weight and 2,2,6,6,7,8,8-heptamethyldecahydro-2H-indeno[4,5-b]furan in an amount of from about 85 to about 99% by weight.

Another embodiment of the present invention relates to a method of improving, enhancing or modifying another fragrance formulation comprising the step of adding the fragrance formulations provided above to the other fragrance formulation.

Another embodiment of the present invention relates to a fragrance product comprising the fragrance formulations provided above.

These and other embodiments of the present invention will be apparent by reading the following specification.

DETAILED DESCRIPTION OF THE INVENTION

The present invention relates to a novel fragrance compound, 2,2,6,6,7,8,8-heptamethyl-3,3a,4,5,5a,6,7,8-octahydro-2H-indeno[4,5-b]furan (Formula I) and its use in perfume formulations, particularly in a perfume formulation that contains 2,2,6,6,7,8,8-heptamethyldecahydro-2H-indeno[4,5-b]furan. The novel fragrance compound of the present invention provides synergistic effect of unexpected and advantageous increase in odor strength and complexity to a perfume formulation that contains 2,2,6,6,7,8,8-heptamethyldecahydro-2H-indeno[4,5-b]furan.

Those with skill in the art will recognize that the compounds of the present invention contain chiral centers, thereby providing a number of stereoisomers of the claimed compounds. The compound of Formula I contains chiral centers at 3a, 5a and 7 positions and includes individual isomers such as, for example, (3aS,5aS,7R)-2,2,6,6,7,8,8-heptamethyl-3,3a,4,5,5a,6,7,8-octahydro-2H-indeno[4,5-b]furan, (3aR,5aS,7R)-2,2,6,6,7,8,8-heptamethyl-3,3a,4,5,5a,6,7,8-octahydro-2H-indeno[4,5-b]furan, (3aS,5aS,7S)-2,2,6,6,7,8,8-heptamethyl-3,3a,4,5,5a,6,7,8-octahydro-2H-indeno[4,5-b]furan, (3aR,5aS,7S)-2,2,6,6,7,8,8-heptamethyl-3,3a,4,5,5a,6,7,8-octahydro-2H-indeno[4,5-b]furan, (3aS,5aR,7R)-2,2,6,6,7,8,8-heptamethyl-3,3a,4,5,5a,6,7,8-octahydro-2H-indeno[4,5-b]furan, (3aR,5aR,7R)-2,2,6,6,7,8,8-heptamethyl-3,3a,4,5,5a,6,7,8-octahydro-2H-indeno[4,5-b]furan, (3aS,5aR,7S)-2,2,6,6,7,8,8-heptamethyl-3,3a,4,5,5a,6,7,8-octahydro-2H-indeno[4,5-b]furan, (3aR,5aR,7S)-2,2,6,6,7,8,8-heptamethyl-3,3a,4,5,5a,6,7,8-octahydro-2H-indeno[4,5-b]furan or any mixtures thereof.

2,2,6,6,7,8,8-Heptamethyldecahydro-2H-indeno[4,5-b]furan represented by Formula II set forth below contains chiral centers at 3a, 5a, 7, 8a and 8b positions:

Formula II

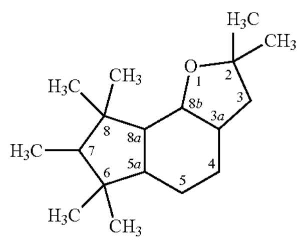

The compound of Formula II includes various individual isomers and any mixtures thereof such as, for example, but not limited to, (3aR,5aR,7R,8aR,8bS)-2,2,6,6,7,8,8-heptamethyldecahydro-2H-indeno[4,5-b]furan, (3aR,5aR,7S,8aR,8bS)-2,2,6,6,7,8,8-heptamethyldecahydro-2H-indeno[4,5-b]furan, (3aR,5aR,8aR,8bS)-2,2,6,6,7,8,8-heptamethyldecahydro-2H-indeno[4,5-b]furan (Structure 1), (3aS,5aR,7R,8aR,8bS)-2,2,6,6,7,8,8-heptamethyldecahydro-2H-indeno[4,5-b]furan, (3aS,5aR,7S,8aR,8bS)-2,2,6,6,7,8,8-heptamethyldecahydro-2H-indeno[4,5-b]furan, (3aS,5aR,8aR,8bS)-2,2,6,6,7,8,8-heptamethyldecahydro-2H-indeno[4,5-b]furan (Structure 2), (3aS,5aR,7R,8aS,8bS)-2,2,6,6,7,8,8-heptamethyldecahydro-2H-indeno[4,5-b]furan, (3aS,5aR,7S,8aS,8bS)-2,2,6,6,7,8,8-heptamethyldecahydro-2H-indeno[4,5-b]furan, (3aS,5aR,8aS,8bS)-2,2,6,6,7,8,8-heptamethyldecahydro-2H-indeno[4,5-b]furan (Structure 3), (3aS,5aR,7R,8aR,8bR)-2,2,6,6,7,8,8-heptamethyldecahydro-2H-indeno[4,5-b]furan, (3aS,5aR,7S,8aR,8bR)-2,2,6,6,7,8,8-heptamethyldecahydro-2H-indeno[4,5-b]furan, (3aS,5aR,8aR,8bR)-2,2,6,6,7,8,8-heptamethyldecahydro-2H-indeno[4,5-b]furan (Structure 4), (3aS,5aR,7R,8aS,8bR)-2,2,6,6,7,8,8-heptamethyldecahydro-2H-indeno[4,5-b]furan (3aS,5aR,7S,8aS,8bR)-2,2,6,6,7,8,8-heptamethyldecahydro-2H-indeno[4,5-b]furan, and (3aS,5aR,8aS,8bR)-2,2,6,6,7,8,8-heptamethyldecahydro-2H-indeno[4,5-b]furan (Structure 5).

It is intended herein that the compounds of the present invention include isomeric mixtures as well as individual isomers that may be separated using techniques known to those having skill in the art. Suitable techniques include chromatography such as high performance liquid chromatography, referred to as HPLC, particularly silica gel chromatography, and gas chromatography trapping known as GC trapping. Yet, commercial versions of such products are mostly offered as mixtures.

2,2,6,6,7,8,8-Heptamethyl-3,3a,4,5,5a,6,7,8-octahydro-2H-indeno[4,5-b]furan (Formula I) can be used alone, in combination with 2,2,6,6,7,8,8-heptamethyldecahydro-2H-indeno[4,5-b]furan (Formula II) or in further combination with additional perfuming compositions, solvents, adjuvants and the like.

The present invention relates to the unexpected and advantageous increase in odor strength and complexity provided by the compound of Formula I to a fragrance formulation containing the compound of Formula II. In a preferred embodiment, the fragrance formulation contains the Formula I compound in an amount of about 0.10% or higher by weight and the Formula II compound in an amount of from about 85 to about 99% by weight. In a more preferred embodiment, the fragrance formulation contains the Formula I compound in an amount of from about 0.1 to about 1% by weight and the Formula II compound in an amount of from about 85 to about 99% by weight. In an even more preferred embodiment, the fragrance formulation contains the Formula I compound in an amount of from about 0.1 to about 1% by weight and the Structure 1 of the Formula II compound in an amount of from about 65 to about 90% by weight, the Structure 2 of the Formula II compound in an amount of from about 0.1 to about 150% by weight and the Structure 3 of the Formula II compound in an amount of from about 1 to about 20% by weight. The fragrance formulation in the even more preferred embodiment has been shown to provide synergistic effect of unexpected and superior desirable fragrance properties. Optionally, additional Formula II isomers such as, for example, but not limited to, (3aS,5aR,8aR,8bR)-2,2,6,6,7,8,8-heptamethyldecahydro-2H-indeno[4,5-b]furan (Structure 4) and/or (3aS,5aR,8aS,8bR)-2,2,6,6,7,8,8-heptamethyldecahydro-2H-indeno[4,5-b]furan (Structure 5), each in an amount of from about 0 to about 5% by weight, may also be included in the fragrance formulation. The present invention has therefore made surprising and unexpected discovery of the synergistic effect achieved by combining the Formula I and Formula II compounds in a fragrance formulation at particular mixing levels.

The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassis, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy] exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone a), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3- one (Methyl Ionone a Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo [7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), 3-[cis-4-(2-methylpropyl)cyclohexyl]propanal (Starfleur), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), (3E)-4-methyldec-3-en-5-one (Veridian), 4-tert-butylcyclohexyL acetate (Vertenex), acetyl cedrene (Vertofix), 3,6/4,6-dimethylcyclohex-3-ene-1-carboxaldehyde (Vertoliff) and (3Z)-1-[(2-methyl-2-propenyl)oxy]-3-hexene (Vivaldie).

As used herein, the term “a” or “an” is understood to mean one or more. The term “a compound” is understood to mean one or more of the compounds represented by Formula I or Formula II as described herein. The preparation of the compounds of the present invention is detailed in the Examples. Materials were purchased from Aldrich Chemical Company unless noted otherwise.

The terms “fragrance formulation”, “fragrance composition”, and “perfume composition” mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising the Formula I compound of the present invention. The fragrance formulation of the present invention is a consumer composition comprising the Formula I and Formula II compounds of the present invention. The fragrance formulation of the present invention comprises a compound of the present invention and further a complementary fragrance compound as defined above.

The terms “fragrance product” and “functional product” mean the same and refer to a consumer product containing a fragrance ingredient that adds fragrance or masks malodor. Fragrance products may include, for example, perfumes, colognes, toilet water, bar soaps, liquid soaps, shower gels, foam baths, cosmetics, personal care and skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric care products such as fabric softeners and fresheners, air care products such as air fresheners and fragrance delivery systems, cosmetic preparations, cleaning products and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. The fragrance product of the present invention contains a compound of the present invention and further a complementary fragrance compound as defined above.

The term “improving” in the phrase “improving, enhancing or modifying a fragrance formulation” is understood to mean raising the fragrance formulation to a more desirable character. The term “enhancing” is understood to mean making the fragrance formulation greater in effectiveness or providing the fragrance formulation with an improved character. The term “modifying” is understood to mean providing the fragrance formulation with a change in character.

The term “olfactory acceptable amount” is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica. Some preferred polymers include polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), or a combination thereof.

When used in a fragrance formulation these ingredients provide additional notes to make a fragrance formulation more desirable and noticeable and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towelettes, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processing, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the formulation of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a formulation of the invention contains a surface active agent or a disinfectant, while in others, the malodor counteractant is present on a fibrous substrate. In many formulations of the invention there is also present a fragrance component which imparts a fragrance to the formulation. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, mmol is understood to be millimole, psi is understood to be pound-force per square inch, and mmHg be millimeters (mm) of mercury (Hg). IFF as used in the examples is understood to mean International Flavors & Fragrances Inc., New York, NY, USA.

Example I

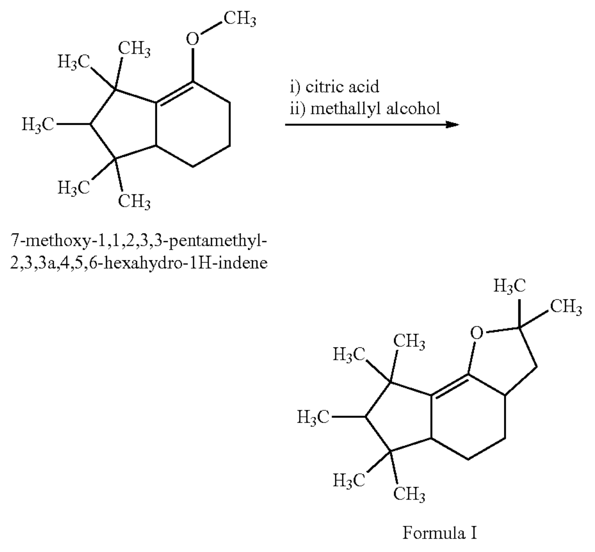

7-methoxy-1,1,2,3,3-pentamethyl-2,3,3a,4,5,6-hexahydro-1H-indene

Formula I

Preparation of 2,2,6,6,7,8,8-Heptamethyl-3,3a,4,5,5a,6,7,8-octahydro-2H-indeno[4,5-b]furan (Formula I): 7-Methoxy-1,1,2,3,3-pentamethyl-2,3,3a,4,5,6-hexahydro-1H-indene was prepared according to a known method (e.g., U.S. Pat. No. 7,312,187). 7-Methoxy-1,1,2,3,3-pentamethyl-2,3,3a,4,5,6-hexahydro-1H-indene (270 g) and citric acid (10 g) were charged to a reaction flask. The reaction mixture was heated to 100° C. Methallyl alcohol (98 g) was added over a period of 1.5 hours while the temperature was raised to 169° C. to distill off the lights. The reaction was quenched with sodium acetate and rushed over to provide the crude product (279 g) having a boiling point of 137° C. at 3 mmHg, which was then purified by distillation to afford 2,2,6,6,7,8,8-heptamethyl-3,3a,4,5,5a,6,7,8-octahydro-2H-indeno[4,5-b]furan (Formula I) (175 g).

$^1H$ NMR (500 MHz, $CDCl_3$) δ: 2.66 (m, 1H), 2.07 (m, 1H), 1.17-2.04 (m, 2H), 1.26-1.88 (m, 2H), 1.17-1.68 (m, 2H), 1.32 (s, 3H), 1.29 (m, 1H), 1.26 (s, 3H), 1.08 (s, 3H), 1.06 (s, 3H), 0.89 (s, 3H), 0.77 (d, J=7.25 Hz, 3H), 0.59 (s, 3H)

2,2,6,6,7,8,8-heptamethyl-3,3a,4,5,5a,6,7,8-octahydro-2H-indeno[4,5-b]furan (Formula I) was described as having weak woody and warm notes.

Example II

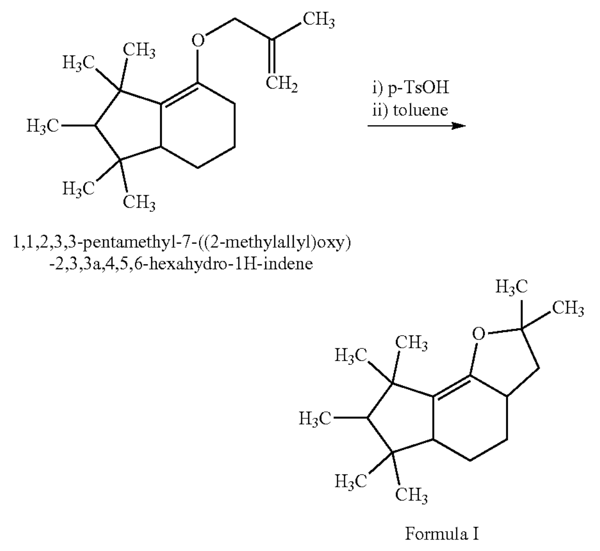

1,1,2,3,3-pentamethyl-7-((2-methylallyl)oxy)-2,3,3a,4,5,6-hexahydro-1H-indene

Formula I

Preparation of 2,2,6,6,7,8,8-Heptamethyl-3,3a,4,5,5a,6,7,8-octahydro-2H-indeno[4,5-b]furan (Formula I): Alternatively, 2,2,6,6,7,8,8-heptamethyl-3,3a,4,5,5a,6,7,8-octahydro-2H-indeno[4,5-b]furan was prepared in the following. 1,1,2,3,3-Pentamethyl-7-((2-methylallyl)oxy)-2,3,3a,4,5,6-hexahydro-1H-indene was prepared according to a known method (e.g., U.S. Pat. No. 7,312,187). p-Toluenesulfonic acid (p-TsOH) (60 g) and toluene (1500 g) were charged to a reaction flask. The reaction mixture was heated to reflux at about 110° C. Heating under reflux was continued while the temperature was slowly increased from about 110 to about 130° C. and the addition of 1,1,2,3,3-pentamethyl-7-((2-methylallyl)oxy)-2,3,3a,4,5,6-hexahydro-1H-indene (3000 g) was completed over a period of 4 hours. The reaction mixture was aged for another 2 hours under reflux at about 130° C. to provide the crude product, which was then purified by fractionation distillation to afford 2,2,6,6,7,8,8-heptamethyl-3,3a,4,5,5a,6,7,8-octahydro-2H-indeno[4,5-b]furan (Formula I) (1950 g) having a boiling point of 130° C. at 2 mmHg.

$^1H$ NMR (500 MHz, $CDCl_3$) δ: 2.66 (m, 1H), 2.07 (m, 1H), 1.17-2.04 (m, 2H), 1.26-1.88 (m, 2H), 1.17-1.68 (m, 2H), 1.32 (s, 3H), 1.29 (m, 1H), 1.26 (s, 3H), 1.08 (s, 3H), 1.06 (s, 3H), 0.89 (s, 3H), 0.77 (d, J=7.25 Hz, 3H), 0.59 (s, 3H)

Example III

Identification of 2,2,6,6,7,8,8-Heptamethyldecahydro-2H-indeno[4,5-b]furan (Formula II) Isomers: 2,2,6,6,7,8,8-Heptamethyldecahydro-2H-indeno[4,5-b]furan (commercially available at IFF) isomers were identified using silica gel chromatography with a Biotage® apparatus.

(3aR,5aR,8aR,8bS)-2,2,6,6,7,8,8-Heptamethyldecahydro-2H-indeno[4,5-b]furan (Structure 1)

$^1H$ NMR (400 MHz, $CDCl_3$) δ: 4.06 (m, 1H), 2.61 (m, 1H), 1.59-1.86 (m, 2H), 1.56-1.83 (m, 2H), 1.14-1.45 (m, 2H), 1.37 (m, 1H), 1.36 (s, 3H), 1.22 (s, 3H), 1.12 (m, 1H), 0.99 (s, 3H), 0.95 (s, 3H), 0.86 (s, 3H), 0.83 (m, 1H), 0.76 (d, J=7.25 Hz, 3H), 0.64 (s, 3H)

(3aR,5aR,8aR,8bS)-2,2,6,6,7,8,8-Heptamethyldecahydro-2H-indeno[4,5-b]furan (Structure 1) was described as having ambery and woody notes.

(3aS,5aR,8aR,8bS)-2,2,6,6,7,8,8-Heptamethyldecahydro-2H-indeno[4,5-b]furan (Structure 2)

$^1H$ NMR (500 MHz, $CDCl_3$) δ: 3.15 (m, 1H), 1.01-1.86 (m, 2H), 1.29-1.75 (m, 2H), 1.01-1.62 (m, 2H), 1.45 (m, 1H), 1.37 (m, 1H), 1.25 (s, 3H), 1.20 (s, 3H), 1.17 (m, 1H), 0.99 (m, 1H), 0.94 (s, 3H), 0.93 (s, 3H), 0.87 (s, 3H), 0.74 (d, J=7.25 Hz, 3H), 0.63 (s, 3H)

(3aS,5aR,8aR,8bS)-2,2,6,6,7,8,8-Heptamethyldecahydro-2H-indeno[4,5-b]furan (Structure 2) was described as having ambery and woody notes.

(3aS,5aR,8aS,8bS)-2,2,6,6,7,8,8-Heptamethyldecahydro-2H-indeno[4,5-b]furan (Structure 3)

$^1H$ NMR (500 MHz, $CDCl_3$) δ: 3.57 (m, 1H), 2.23 (m, 1H), 1.99 (m, 1H), 1.33-1.86 (m, 2H), 1.75 (m, 1H), 1.24-1.74 (m, 2H), 0.92-1.59 (m, 2H), 1.35 (m, 1H), 1.29 (s, 3H), 1.23 (s, 3H), 1.09 (s, 3H), 1.00 (s, 3H), 0.93 (s, 3H), 0.82 (s, 3H), 0.71 (d, J=7.25 Hz, 3H)

(3aS,5aR,8aS,8bS)-2,2,6,6,7,8,8-Heptamethyldecahydro-2H-indeno[4,5-b]furan (Structure 3) was described as having ambery, woody and dusty notes.

(3aS,5aR,8aR,8bR)-2,2,6,6,7,8,8-Heptamethyldecahydro-2H-indeno[4,5-b]furan (Structure 4)

$^1H$ NMR (600 MHz, $CDCl_3$) δ: 4.03 (m, 1H), 1.87 (m, 1H), 1.37-1.79 (m, 2H), 1.54-1.61 (m, 2H), 1.36-1.53 (m, 2H), 1.52 (m, 1H), 1.39 (m, 1H), 1.34 (s, 3H), 1.27 (m, 1H), 1.19 (s, 3H), 0.96 (s, 3H), 0.89 (s, 3H), 0.85 (s, 3H), 0.76 (d, J=7.25 Hz, 3H), 0.59 (s, 3H)

(3aS,5aR,8aR,8bR)-2,2,6,6,7,8,8-Heptamethyldecahydro-2H-indeno[4,5-b]furan (Structure 4) was described as having weak, ambery and woody notes.

(3aS,5aR,8aS,8bR)-2,2,6,6,7,8,8-Heptamethyldecahydro-2H-indeno[4,5-b]furan (Structure 5)

$^1H$ NMR (500 MHz, $CDCl_3$) δ: 4.06 (m, 1H), 2.29 (m, 1H), 2.06 (m, 1H), 1.77 (m, 2H), 1.27-1.63 (m, 5H), 1.28 (m, 1H), 1.25 (s, 3H), 1.10 (s, 3H), 0.99 (s, 3H), 0.91 (s, 3H), 0.89 (s, 3H), 0.80 (s, 3H), 0.76 (d, J=7.25 Hz, 3H)

(3aS,5aR,8aS,8bR)-2,2,6,6,7,8,8-Heptamethyldecahydro-2H-indeno[4,5-b]furan (Structure 5) was described as having weak, ambery and woody notes.

Example IV

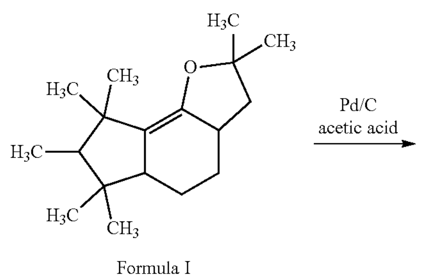

Formula I

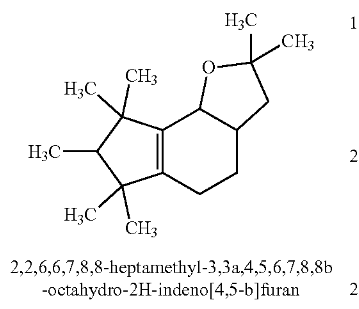

2,2,6,6,7,8,8-heptamethyl-3,3a,4,5,6,7,8,8b-octahydro-2H-indeno[4,5-b]furan

Preparation of 2,2,6,6,7,8,8-Heptamethyl-3,3a,4,5,6,7,8,8b-octahydro-2H-indeno[4,5-b]furan (Formula III): The compound of Formula I (prepared as the above, 40 g), palladium on carbon catalyst (Pd/C, 0.4 g) and acetic acid (2 g) were charged to an autoclave and purged three times with nitrogen followed by three times with hydrogen. The reaction mixture was heated to about 120° C. and pressurized to about 300 psi. The reaction conditions were maintained till the hydrogen uptake was complete. The obtained crude product was further purified with filtration to provide 2,2,6,6,7,8,8-heptamethyl-3,3a,4,5,6,7,8,8b-octahydro-2H-indeno[4,5-b]furan (Formula III) (36 g).

$^1$H NMR (600 MHz, $CDCl_3$) δ: 4.34 (d, J=5.85 Hz, 1H), 2.26 (m, 1H), 1.81-1.96 (m, 2H), 1.50-1.90 (m, 2H), 1.46-1.66 (m, 2H), 1.51 (m, 1H), 1.29 (s, 3H), 1.24 (s, 3H), 1.04 (s, 3H), 1.01 (s, 3H), 0.94 (s, 3H), 0.87 (s, 3H), 0.87 (d, J=7.35 Hz, 3H)

2,2,6,6,7,8,8-Heptamethyl-3,3a,4,5,6,7,8,8b-octahydro-2H-indeno[4,5-b]furan (Formula III) was described as having moderate amber, woody and warm notes.

Example V

The fragrance properties of fragrance formulations containing the Formula II compound with the addition of the Formula I compound at different levels (O % by weight) were evaluated using (i) odor profile; (ii) odor strength ("Strength") of 0 to 10, where 0=none, 1=very weak, 5=moderate, 10=extremely strong; and (iii) level of complexity ("Complexity"), where 0=none, 1=very low, 5=moderate, 10=extremely high. Evaluation is reported in the following:

| | | Formula II Isomers (Structure) | | | | | | |
|---|---|---|---|---|---|---|---|---|
| Sample | Formula I | 1 | 2 | 3 | 1, 2&3 | Odor Profile | Strength | Complexity |
| 1 | 0 | 71.09 | 0 | 22.15 | 93.24 | Weak and plain with woody but metallic characters. Less diffusive, less performing. Lacking the warm, ambery and pleasant characters. | 3 | 1 |
| 2 | 0 | 81.52 | 0.14 | 11.97 | 93.36 | Weak and plain with woody but metallic characters. Less diffusive, less performing. Lacking the warm, ambery and pleasant characters. | 3 | 1 |
| 3 | 0.06 | 78.49 | 1.38 | 14.9 | 94.77 | Not complex, metallic character dominated and overpowered the ambery note. | 7 | 5 |
| 4 | 0.14 | 86.10 | 0.52 | 7.80 | 94.42 | Strong, warm, ambery and woody, performing | 7 | 10 |
| 5 | 0.18 | 81.50 | 0.40 | 11.22 | 93.12 | Strong, warm, ambery and woody, performing | 7 | 10 |
| 6 | 0.35 | 74.03 | 7.08 | 13.92 | 95.03 | Very powerful, high impact, warm, ambery and woody, performing | 10 | 10 |
| 7 | 0.46 | 73.57 | 6.04 | 14.21 | 93.82 | Very powerful, high impact, warm, ambery and woody, performing | 10 | 10 |
| 8 | 0.52 | 72.61 | 5.46 | 17.74 | 95.81 | Very powerful, high impact, warm, ambery and woody, performing | 10 | 10 |
| 9 | 0.58 | 70.71 | 10.13 | 12.56 | 93.40 | Very powerful, high impact, warm, ambery and woody, performing | 9 | 10 |
| 10 | 0.59 | 85.59 | 2.05 | 5.68 | 93.32 | Very powerful, high impact, warm, ambery and woody, performing | 9 | 10 |
| 11 | 0.65 | 83.32 | 1.97 | 7.27 | 92.56 | Very powerful, high impact, warm, ambery and woody, performing | 9 | 10 |
| 12 | 0.71 | 73.42 | 3.84 | 15.91 | 93.17 | Very powerful, high impact, warm, ambery and woody, performing | 9 | 10 |

-continued

| Sample | Formula I | Formula II Isomers (Structure) 1 | 2 | 3 | 1, 2&3 | Odor Profile | Strength | Complexity |
|---|---|---|---|---|---|---|---|---|
| 13 | 0.78 | 79.53 | 2.51 | 12.45 | 94.49 | Very powerful, high impact, warm, ambery and woody, performing | 9 | 10 |
| 14 | 0.91 | 74.52 | 3.96 | 13.15 | 91.63 | Strong, warm, ambery and woody, performing | 8 | 10 |
| 15 | 1.02 | 73.18 | 0.66 | 18.45 | 92.29 | Not complex, metallic character started to dominate and overpower the ambery note. | 8 | 5 |
| 16 | 1.35 | 71.95 | 3.83 | 15.54 | 91.32 | Strong with unpleasant characters such as fatty, oily, less fresh, less amber and more green. The metallic character dominated the odor profile | 8 | 5 |
| 17 | 1.71 | 73.17 | 3.99 | 12.59 | 89.75 | Strong with unpleasant characters such as fatty, oily, less fresh, less amber and more green. The metallic character dominated the odor profile | 8 | 5 |
| 18 | 2.02 | 72.8 | 3.98 | 12.53 | 89.31 | Strong with unpleasant characters such as fatty, oily, less fresh, less amber and more green. The metallic character dominated the odor profile | 8 | 5 |

The above evaluation yielded unexpected finding, samples 4-18 were surprisingly superior to samples 1-3. An amount of about ~0.1% or higher by weight of the Formula I compound was required for the fragrance formulations to provide desirable fragrance properties. Specifically, a fragrance formulation contains the Formula I compound in an amount of about 0.1% or higher by weight and the Formula II compound in an amount of from about 85 to about 99% by weight provided desirable fragrance properties. More specifically, a fragrance formulation contains the Formula I compound in an amount of from about 0.1 to about 1% by weight, the Structure 1 of the Formula II compound in an amount of from about 65 to about 90% by weight, the Structure 2 of the Formula II compound in an amount of from about 0.1 to about 15% by weight and the Structure 3 of the Formula II compound in an amount of from about 1 to about 20% by weight provided synergistic effect of unexpected and superior desirable fragrance properties.

In contrast, when an analog of the Formula I compound, 2,2,6,6,7,8,8-heptamethyl-3,3a,4,5,6,7,8,8b-octahydro-2H-indeno[4,5-b]furan (Formula III) (0.11% by weight), was added to a fragrance formulation that contained the Formula II compound, no synergistic fragrance effect was obtained.

Thus, the present invention has made surprising and unexpected discovery of the synergistic effect achieved by combining the Formula I and Formula II compounds in a fragrance formulation at particular mixing levels.

Example VI

The fragrance formula exemplified as follows demonstrates that a fragrance formulation containing the Formula I and Formula II compounds provides unexpected and superior synergistic fragrance effect. The Formula I/Formula II containing formula contains the Formula I compound in an amount of 0.46% by weight, the Structure 1 of the Formula II compound in an amount of 73.570% by weight, the Structure 2 of the Formula II compound in an amount of 6.04% by weight and the Structure 3 of the Formula II compound in an amount of 14.210% by weight. The accord exhibits warm, ambery and woody notes, yielding a linear odor and volume over time with extended substantivity of strong performing, pleasant, clean and ambery notes.

| Ingredients | Parts* − | Parts* + |
|---|---|---|
| BASIL OIL | 30.00 | 30.00 |
| BERGAMOT OIL CP BERGAPTFREE | 150.00 | 150.00 |
| COUMARIN | 30.00 | 30.00 |
| DIPROPYLENE GLYCOL | 87.00 | 37.00 |
| EUGENOL NAT EX CLOVE LEAF OIL | 30.00 | 30.00 |
| HEXADECANOLIDE | 350.00 | 350.00 |
| ISO BUTYL QUINOLINE | 3.00 | 3.00 |
| METH IONONE GAMMA A TOCO | 30.00 | 30.00 |
| FORMULA I/FORMULA II | — | 50.00 |
| DIETHYL PHTHALATE | 50.00 | — |
| PATCHOULI OIL LIGHT BLO | 30.00 | 30.00 |
| VERTOFIX COEUR | 200.00 | 200.00 |
| VETIVER OIL HAITI | 60.00 | 60.00 |
| TOTAL | 1000.00 | 1000.00 |

*"+" represents a Formula I/Formula II containing formula; and "−"represents a Formula I/Formula II non-containing formula

What is claimed is:

1. A compound, 2,2,6,6,7,8,8-heptamethyl-3,3a,4,5,5a,6,7,8-octahydro-2H-indeno[4,5-b]furan.

2. A fragrance formulation comprising 2,2,6,6,7,8,8-heptamethyl-3,3a,4,5,5a,6,7,8-octahydro-2H-indeno[4,5-b]furan.

3. The fragrance formulation of claim 2 further comprising 2,2,6,6,7,8,8-heptamethyldecahydro-2H-indeno[4,5-b]furan.

4. The fragrance formulation of claim 3, wherein 2,2,6,6,7,8,8-heptamethyldecahydro-2H-indeno[4,5-b]furan comprises an isomer selected from the group consisting of (3aR,5aR,8aR,8bS)-2,2,6,6,7,8,8-heptamethyldecahydro-2H-indeno[4,5-b]furan;

(3aS,5aR,8aR,8bS)-2,2,6,6,7,8,8-heptamethyldecahydro-2H-indeno[4,5-b]furan;

(3aS,5aR,8aS,8bS)-2,2,6,6,7,8,8-heptamethyldecahydro-2H-indeno[4,5-b]furan;

(3aS,5aR,8aR,8bR)-2,2,6,6,7,8,8-heptamethyldecahydro-2H-indeno[4,5-b]furan;

(3aS,5aR,8aS,8bR)-2,2,6,6,7,8,8-heptamethyldecahydro-2H-indeno[4,5-b]furan; and a mixture thereof.

5. The fragrance formulation of claim 4, wherein 2,2,6,6,7,8,8-heptamethyl-3,3a,4,5,5a,6,7,8-octahydro-2H-indeno[4,5-b]furan is present in an amount of about 0.1% or higher by weight and 2,2,6,6,7,8,8-heptamethyldecahydro-2H-indeno[4,5-b]furan is present in an amount of from about 85 to about 99% by weight.

6. The fragrance formulation of claim 5, wherein 2,2,6,6,7,8,8-heptamethyl-3,3a,4,5,5a,6,7,8-octahydro-2H-indeno[4,5-b]furan is present in an amount of from about 0.1 to about 1% by weight; and wherein 2,2,6,6,7,8,8-heptamethyldecahydro-2H-indeno[4,5-b]furan comprises (3aR,5aR,8aR,8bS)-2,2,6,6,7,8,8-heptamethyldecahydro-2H-indeno[4,5-b]furan in an amount of from about 65 to about 90% by weight;

(3aS,5aR,8aR,8bS)-2,2,6,6,7,8,8-heptamethyldecahydro-2H-indeno[4,5-b]furan in an amount of from about 0.1 to about 15% by weight; and (3aS,5aR,8aS,8bS)-2,2,6,6,7,8,8-heptamethyldecahydro-2H-indeno[4,5-b]furan in an amount of from about 1 to about 20% by weight.

7. The fragrance formulation of claim 2 further comprising a polymer.

8. The fragrance formulation of claim 7, wherein the polymer is selected from the group consisting of polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde) and a combination thereof.

9. A method of improving, enhancing or modifying a first fragrance formulation comprising the step of adding to the first fragrance formulation a second fragrance formulation, wherein the second fragrance formulation comprises 2,2,6,6,7,8,8-heptamethyl-3,3a,4,5,5a,6,7,8-octahydro-2H-indeno[4,5-b]furan.

10. The method of claim 9, wherein the second fragrance formulation further comprises 2,2,6,6,7,8,8-heptamethyldecahydro-2H-indeno[4,5-b]furan.

11. The method of claim 10, wherein 2,2,6,6,7,8,8-heptamethyldecahydro-2H-indeno[4,5-b]furan comprises an isomer selected from the group consisting of (3aR,5aR,8aR,8bS)-2,2,6,6,7,8,8-heptamethyldecahydro-2H-indeno[4,5-b]furan;

(3aS,5aR,8aR,8bS)-2,2,6,6,7,8,8-heptamethyldecahydro-2H-indeno[4,5-b]furan;

(3aS,5aR,8aS,8bS)-2,2,6,6,7,8,8-heptamethyldecahydro-2H-indeno[4,5-b]furan;

(3aS,5aR,8aR,8bR)-2,2,6,6,7,8,8-heptamethyldecahydro-2H-indeno[4,5-b]furan;

(3aS,5aR,8aS,8bR)-2,2,6,6,7,8,8-heptamethyldecahydro-2H-indeno[4,5-b]furan; and a mixture thereof.

12. The method of claim 11, wherein 2,2,6,6,7,8,8-heptamethyl-3,3a,4,5,5a,6,7,8-octahydro-2H-indeno[4,5-b]furan is present in an amount of about 0.1% or higher by weight of the second fragrance formulation and 2,2,6,6,7,8,8-heptamethyldecahydro-2H-indeno[4,5-b]furan is present in an amount of from about 85 to about 99% by weight of the second fragrance formulation.

13. The method of claim 12, wherein 2,2,6,6,7,8,8-heptamethyl-3,3a,4,5,5a,6,7,8-octahydro-2H-indeno[4,5-b]furan is present in an amount of from about 0.1 to about 1% by weight of the second fragrance formulation; and wherein 2,2,6,6,7,8,8-heptamethyldecahydro-2H-indeno[4,5-b]furan comprises (3aR,5aR,8aR,8bS)-2,2,6,6,7,8,8-heptamethyldecahydro-2H-indeno[4,5-b]furan in an amount of from about 65 to about 90% by weight of the second fragrance formulation;

(3aS,5aR,8aR,8bS)-2,2,6,6,7,8,8-heptamethyldecahydro-2H-indeno[4,5-b]furan in an amount of from about 0.1 to about 15% by weight of the second fragrance formulation; and (3aS,5aR,8aS,8bS)-2,2,6,6,7,8,8-heptamethyldecahydro-2H-indeno[4,5-b]furan in an amount of from about 1 to about 20% by weight of the second fragrance formulation.

14. A fragrance product containing the compound of claim 1.

15. The fragrance product of claim 14 further containing 2,2,6,6,7,8,8-heptamethyldecahydro-2H-indeno[4,5-b]furan.

16. The fragrance product of claim 15, wherein 2,2,6,6,7,8,8-heptamethyldecahydro-2H-indeno[4,5-b]furan comprises an isomer selected from the group consisting of (3aR,5aR,8aR,8bS)-2,2,6,6,7,8,8-heptamethyldecahydro-2H-indeno[4,5-b]furan;

(3aS,5aR,8aR,8bS)-2,2,6,6,7,8,8-heptamethyldecahydro-2H-indeno[4,5-b]furan;

(3aS,5aR,8aS,8bS)-2,2,6,6,7,8,8-heptamethyldecahydro-2H-indeno[4,5-b]furan;

(3aS,5aR,8aR,8bR)-2,2,6,6,7,8,8-heptamethyldecahydro-2H-indeno[4,5-b]furan;

(3aS,5aR,8aS,8bR)-2,2,6,6,7,8,8-heptamethyldecahydro-2H-indeno[4,5-b]furan; and a mixture thereof.

17. The fragrance product of claim 14, wherein the fragrance product is selected from the group consisting of a perfume, a cologne, toilet water, a bar soap, a liquid soap, a shower gel, a foam bath, a cosmetic, a personal care product, a skin care product, a hair care product, a deodorant, an antiperspirant, a feminine care product, a baby care product, a family care product, a fabric product, an air care product, a fragrance delivery system, a cosmetic preparation, a cleaning product, a disinfectant, a washing agent, a dental and oral hygiene product, a health care and nutritional product and a food product.

* * * * *